United States Patent [19]

Crilly

[11] Patent Number: 5,046,501
[45] Date of Patent: Sep. 10, 1991

[54] ATHEROSCLEROTIC IDENTIFICATION

[75] Inventor: Richard Crilly, Ontario, Canada

[73] Assignee: Wayne State University, Detroit, Mich.

[21] Appl. No.: 298,576

[22] Filed: Jan. 18, 1989

[51] Int. Cl.⁵ .............................................. A61B 6/00
[52] U.S. Cl. ....................................... 128/665; 606/3
[58] Field of Search ............................... 128/395–398, 128/303.1, 633, 664, 665; 606/3

[56] References Cited

U.S. PATENT DOCUMENTS

| | | | |
|---|---|---|---|
| 4,479,499 | 10/1984 | Alfano | 128/665 |
| 4,556,057 | 12/1985 | Hiruma et al. | 128/395 |
| 4,648,892 | 3/1987 | Kittrell et al. | 128/398 |
| 4,768,513 | 9/1988 | Suzuki | 128/665 |
| 4,785,806 | 11/1988 | Deckelbaum | 128/666 |

OTHER PUBLICATIONS

Kittrell et al., "Diagnosis of Fibrous Arterial Atherosclerosis Using Fluorescence", Applied Optics, vol. 24, No. 15, Aug. 1985, pp. 2280–2281.
Scientific Tables, "Statistical Methods", pp. 145–196, Document A, Geigy, Seventh Edition, 1973.

*Primary Examiner*—Ruth S. Smith
*Attorney, Agent, or Firm*—Kenneth I. Kohn

[57] ABSTRACT

A method of identifying atherosclerotic plaque versus structurally viable tissue includes the steps of emitting a fluorescent beam at a single excitation wavelength of between 350 and 390 nm at a tissue and detecting and quantifying the emission spectrum of the emitted beam at critical points chosen to optimize the difference between atherosclerotic plaque and structurally viable tissue. The presence of the atherosclerotic plaque is distinguished from structurally viable tissue by the presence or absence of the intensity of emissions at the critical points of optimum distinguishing wavelengths.

4 Claims, 7 Drawing Sheets

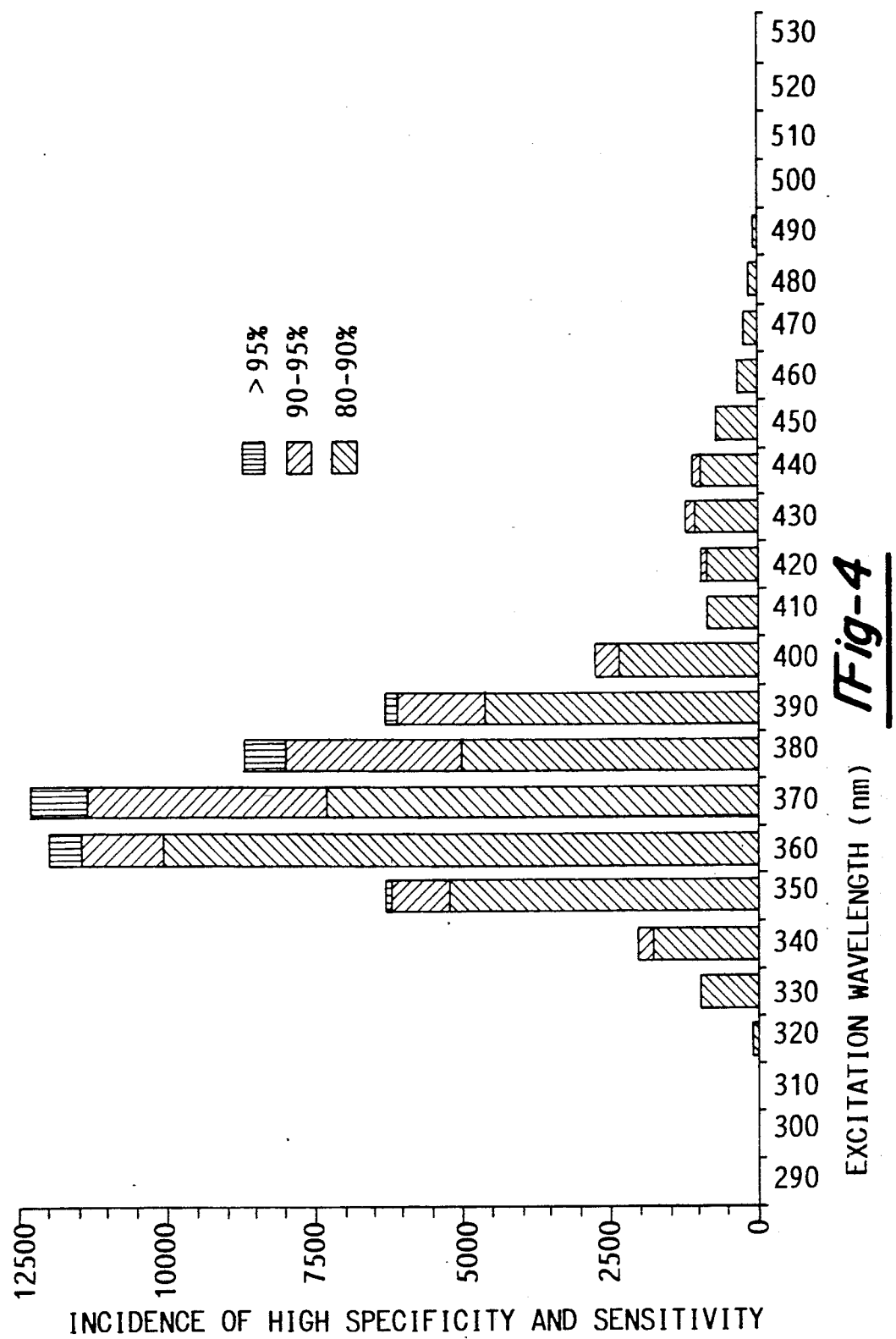

ATHEROSCLEROTIC IDENTIFICATIONS

BACKGROUND OF THE INVENTION

The potential use of in vivo fluorescent measurement for tissue identification has been an active field of research. In the field of oncology, Profio reported on the localization of lung tumors using tumor specific fluorescence porphyrin dies. Profio A. E. et al, Fluorescent Bronchoscopy for Localization of Carcinoma In Situ, Medical Physics. The potential application of this technology to cardiology became apparent with the discovery that porphyrin derivatives were selectively taken up by atherosclerotic plaques. Spears, J. R. et al Fluorescence of Experimental Atheromatosus Plaques with Hematoporphyrin Derivatives, J. Clin. In Vest. 71, page 395 [1938]. Problems arose because the hematoporphyrin drug had a number of adverse side effects.

It has been observed that plaque in normal tissue has autofluorescence, as observed in post-mortem arterial samples by Kittrell C. et al, Diagnosis of Fibrous Arterial Atherosclerosis Using Fluorescence, Lasers in Medical Science [1987]. Kitrell's observation was based mainly on an experimental artifact but nonetheless provided the impetus for further studies which indicated other differences in the autofluorescence spectrum that could be used for plaque identification. Anderson, P. S., Diagnosis of Arterial Atherosclerosis using Laser-induced Fluorescence, Lasers in Medical Science, 2 p. 261, [1987]; Clark, R. H. et al., Spectroscopitc Characterization of Cardiovascular Tissue., Lasers in Surgery and Medicine, 8 p. 45, [1988]; Deckelbaum, L. I. et al., In-vivo Fluorescence Spectroscopy of Normal and Atherosclerotic Arteries, SPIE V. 906 Optical Fibers in Medicine III [1988]; Leon M. B. et al, Human Arterial Surface Fluorescence; Atherosclerotic Plaque Identifiecation and Effects to Laser Atheroma Ablation, JACC, 12: 1p.94, [1988]. Among these studies included in vivo work that showed that the autofluorescence signal, even though being quite low, was sufficient for spectral discrimination.

The present invention utilized a novel approach to spectral analysis of normal structural tissue versus atherosclerotic plaque to determine a specific method of identifying atherosclerotic plaque from structurally viable tissue. The present invention further provides a means of discriminating arterial tissue surface from arterial tissue surface from which plaque has been removed. Finally, the present invention provides a base from which a more indepth identification of chemical differences can be made between atherosclerotic plaque and structural viable tissue types.

SUMMARY OF THE INVENTION

The present invention provides a method of identifying atherosclerotic plaque from structural viable arterial wall tissue, the method including the steps of emitting a fluorescent beam at a single excitation wavelength of between 350 and 390 nm at the arterial wall, detecting and quantifying the emission spectrum of the emitted beam at critical points chose to optimize the difference between atherosclerotic plaque and structurally viable tissue, and distinguishing the presence of atherosclerotic plaque from structurally viable tissue by the presence or absence of the quantity of emission intensities at the critical points in the emission spectra.

BRIEF DESCRIPTION OF THE DRAWINGS

Other advantages of the present invention will be readily appreciated as the same becomes better understood by reference to the following detailed description when considered in connection with the accompanying drawings wherein:

FIG. 1b is a two dimensional contour plot of the data by FIG. 1a;

FIG. 2b is a two dimensional contour plot of the data in FIG. 2a;

FIG. 3b is a two dimensional contour plot of the data in FIG. 3a; and

FIG. 4 is a histogram plotting incidence of high specificity and sensitivity versus excitation wavelength (nm).

DETAILED DESCRIPTION OF THE INVENTION

Figure 1A:
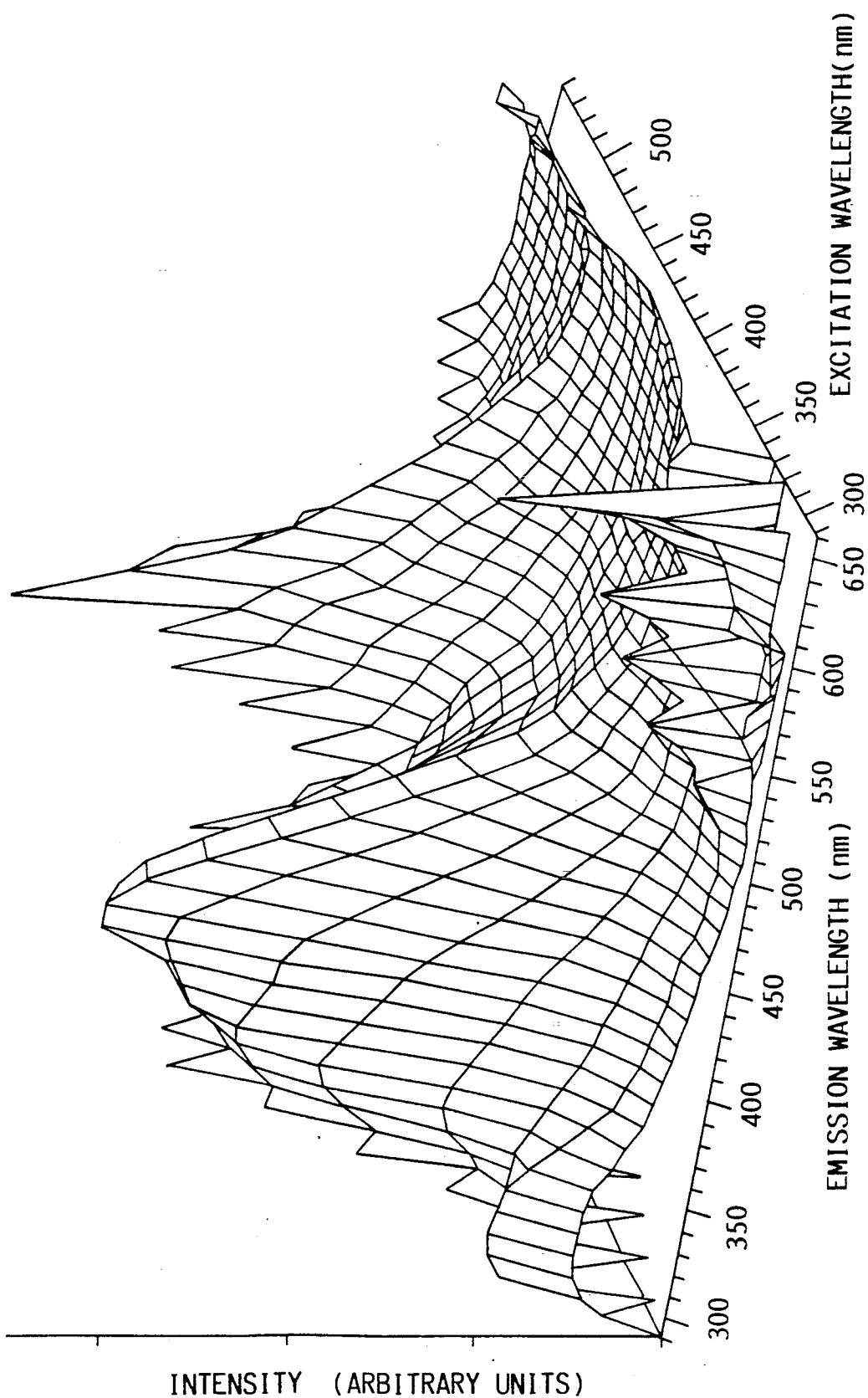
FIG. 1a is a three dimensional contour plot of a typical fluorometer measurement of a normal human aorta.

In accordance with the present invention, there is provided a method of identifying atherosclerotic plaque from surrounding structurally viable tissue. Structurally viable tissue is meant to mean normal structural tissue not having atherosclerotic plaque thereon and tissue having had atherosclerotic plaque removed therefrom, leaving the structurally viable media of the tissue exposed. Accordingly, during an angioplasty procedure, the present invention can be utilized to identify atherosclerotic plaque prior to ablation. The invention can further be used in a feedback mechanism to determine when ablation should be stopped by the exposure of the media below the atherosclerotic plaque.

Generally, the method accomplished in accordance with the present invention includes the steps of emitting a fluorescent beam at a single excitation wavelength of between 350 and 390 nm at an arterial wall. The tissue may be the inner wall of a vessel, such as the femoral artery or a vessel presenting a more serquitious path, such as the vessels within the heart. Experimentation, as discussed herein after, has shown that there is an optimum excitation wavelength range between 350 and 390 nm for the identification of the atherosclerotic plaque. The emission spectrum of the emitted beam is detected and quantified at critical points of optimum distinguishing wavelengths from atherosclerotic plaque and structural viable tissue. The emission spectrum is detected by a fluorescence detection system commonly used in the art. However, for the purposes of this invention, fluorescence emission from the tissue being inspected need only be determined at specific critical points.

It is preferred that the fluorescent beam is emitted from a laser. Most lasers only produce light at one wavelength thus greatly reducing the number of potential fluorescence peaks available for discrimination.

It has been found, pursuant to the present invention, that both atherosclerotic plaque and structurally viable tissue emit fluorescence at peaks or at least provide detectable aberrations in a fluorescent spectrum when excited at wavelengths between 350 and 390 nm such that the peaks or the spectra of aberrations of atherosclerotic plaque or structurally viable tissue are discernible or distinguishable with sensitivity and specificity over 95%. It is therefore a step of the present inventive method to detect and quantify the emission spectrum of the emitted beam at those critical points of optimum distinguishing emission, such optimums being characteristic of atherosclerotic plaque and structurally viable tissue. Finally, the presence of atherosclerotic plaque is distinguished from structural viable tissue by the presence or absence of the quantity of emissions at the critical points of optimum distinguishing wavelengths. That is, if there is a quantifiably greater emission at those critical points of optimum emission characteristic of atherosclerotic plaque and a low value at those critical point of emission characteristic of normal structural tissue, then the tissue can be characterized as atherosclerotic plaque. If the opposite quantitation is made, then the tissue can be characterized as structurally viable tissue.

Experimentation has determined that the optimum distinguishing emission from the atherosclerotic plaque peaks are at 340 :380 nm (excitation wavelength:emission wavelength) in the excitation emission plane. The optimum distinguishing emission from normal structural tissue peaks are at 360:430 nm in the excitation emission plane. However, applicant has found other distinguishing artifacts characteristic of artherosclerotic plaque at 600 and 570 nm and normal tissue at 480 and 500 nm using an excitation wavelength 370 nm.

EXPERIMENTAL EVIDENCE

Eight human aortas from specimens ranging between 15 months and 70 years were obtained within 18 hours of death. The tissues were examined for an artifact caused by hemoglobin staining and 58 representative samples of different levels of plaque formation were dissected out. These samples were then classified based on their type of diseased development as normal, raised yellow plaque, raised white plaque, calcified plaque and hemoragic or necrotic plaque. Hemoglobin stained samples were scanned in order to become familiar with the effect of such staining. Hemoragic plaque was not included in the statistical analysis since its fluorescent signal is either extremely low or completely absent, a property that in itself can be used to identify this class of plaque.

Fluorescence scans were obtained using a Gilford Fluoro IV grating fluorometer interfaced with IBM AT Computer. This allowed the automatic scanning of any combination of excitation or emission wavelengths between 200 and 800 nm at 10 nm intervals. Calibration measurements were made with a flat black aluminum mounting assembly submerged in saline in an optical grade glass cuvette.

There are a number of artifacts in the spectrum that prevent spectral analysis at certain wavelengths. The artifacts are identified from the blank measurement and arbitrarily set to zero when they resulted in an intensity greater than an arbitrarily chosen value of 10. Other ghosts or imperfections of the grating were observed and were dealt with accordingly in the analysis.

Samples were mounted on a specially made holder at 45° to excitation beam and emission detector optical axis, placed in a cuvette, and immersed in saline. The sample area actually tested resembles an elipse that is 8×15 mm.

The fluorescent signal was initially scanned over the entire 290 to 800 nm range for both the excitation and emission wavelengths. Examination of the initial data indicated no large features of interest in the range outside the excitation wavelength range of 290 to 560 nm and emission wavelength of 290 to 660 nm. Accordingly, the number of wavelengths scanned was reduced to lower the time required to do a complete sample scan.

Diseased tissue, normal tissue, and tissues with the plaque stripped off structurally sound media were examined. This final type of tissue is significant for the use of the present invention with laser angioplasty application in that not only should the system identify healthy intima, but the system should also recognize intact media after superficial plaque has been removed.

Figure 1B:
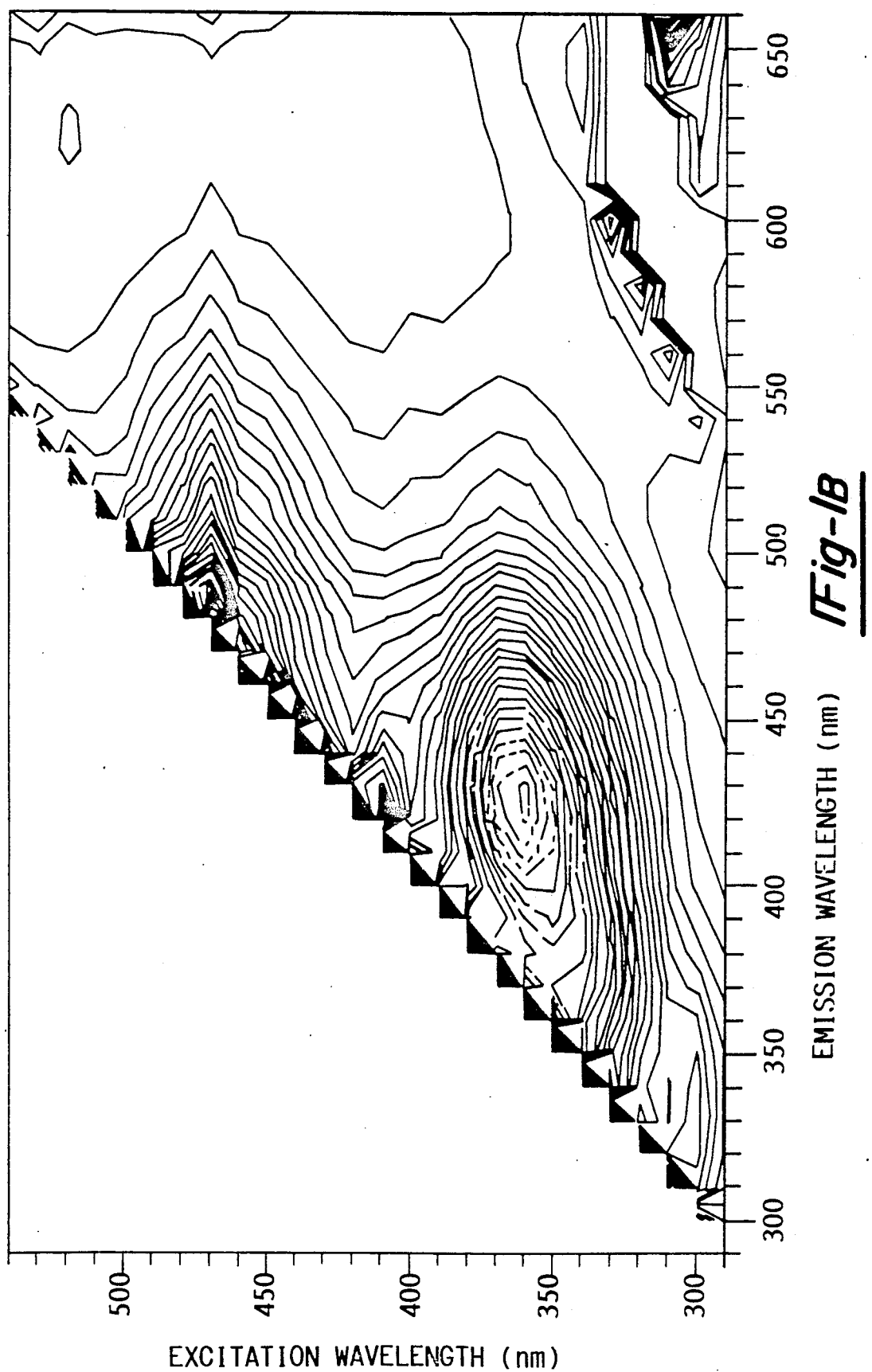
Figure 2A:
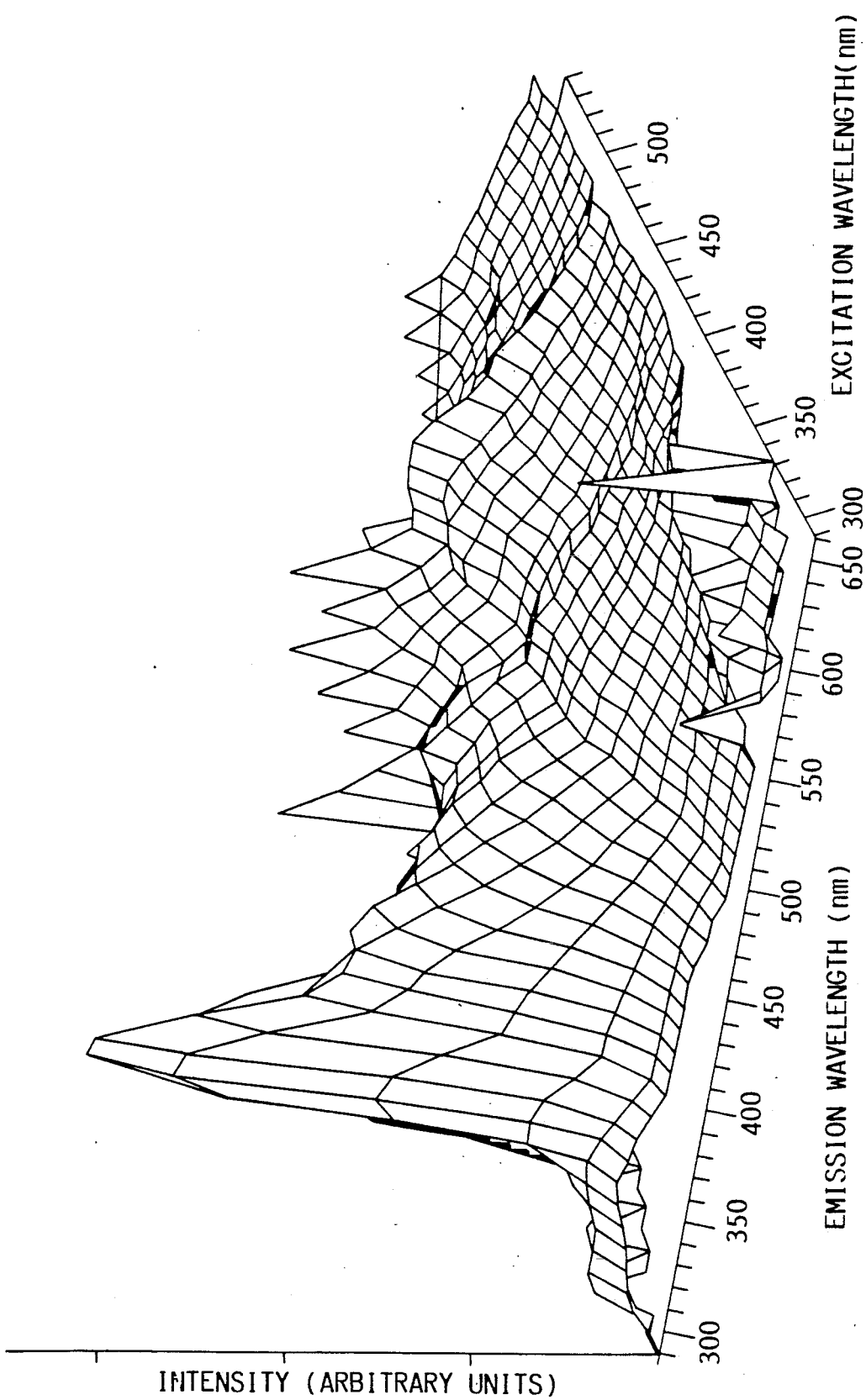
FIG. 2a is a three dimensional contour plot of a typical fluorometric measurement of raised white plaque on a human aorta.
Figure 2B:
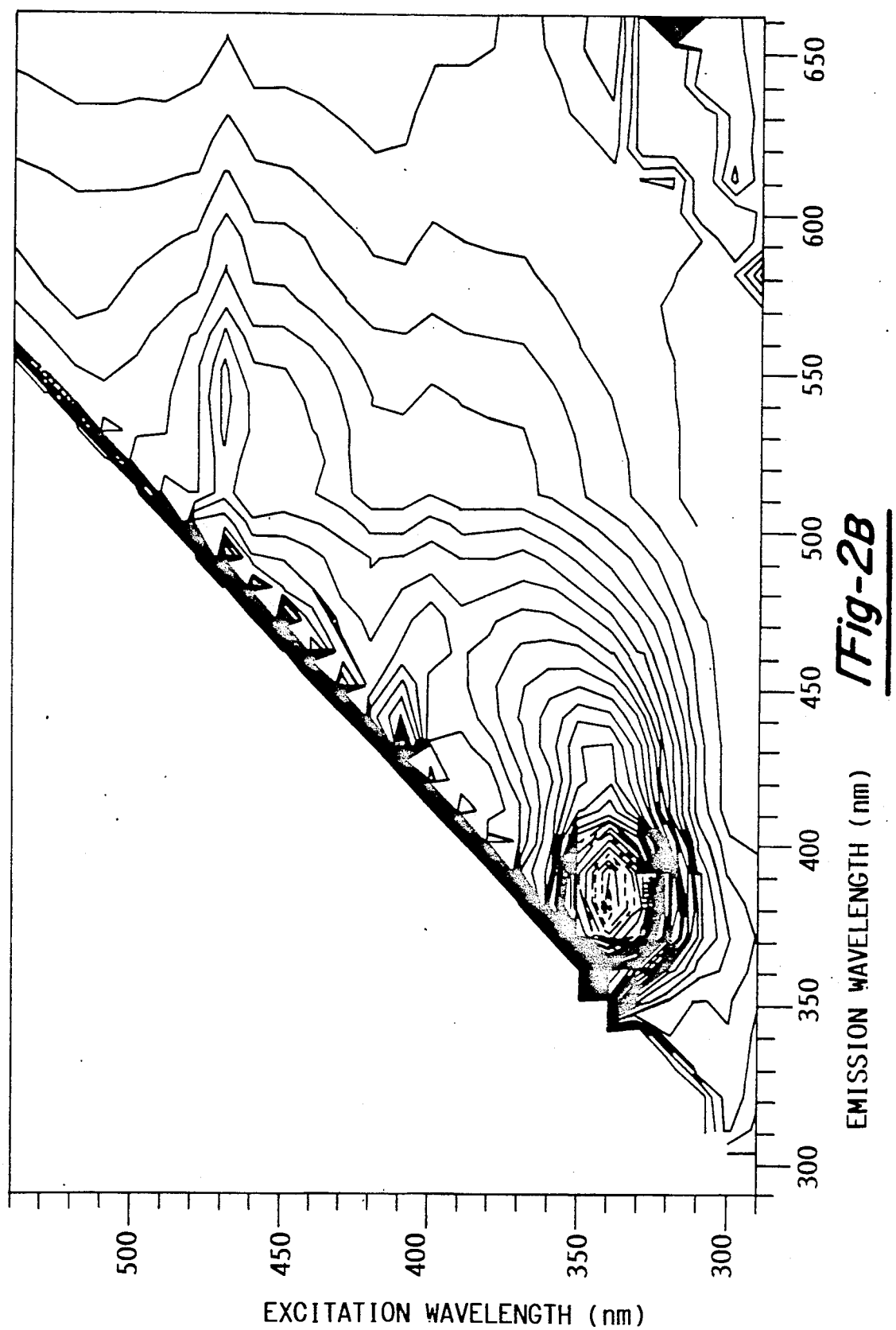
Figure 3A:
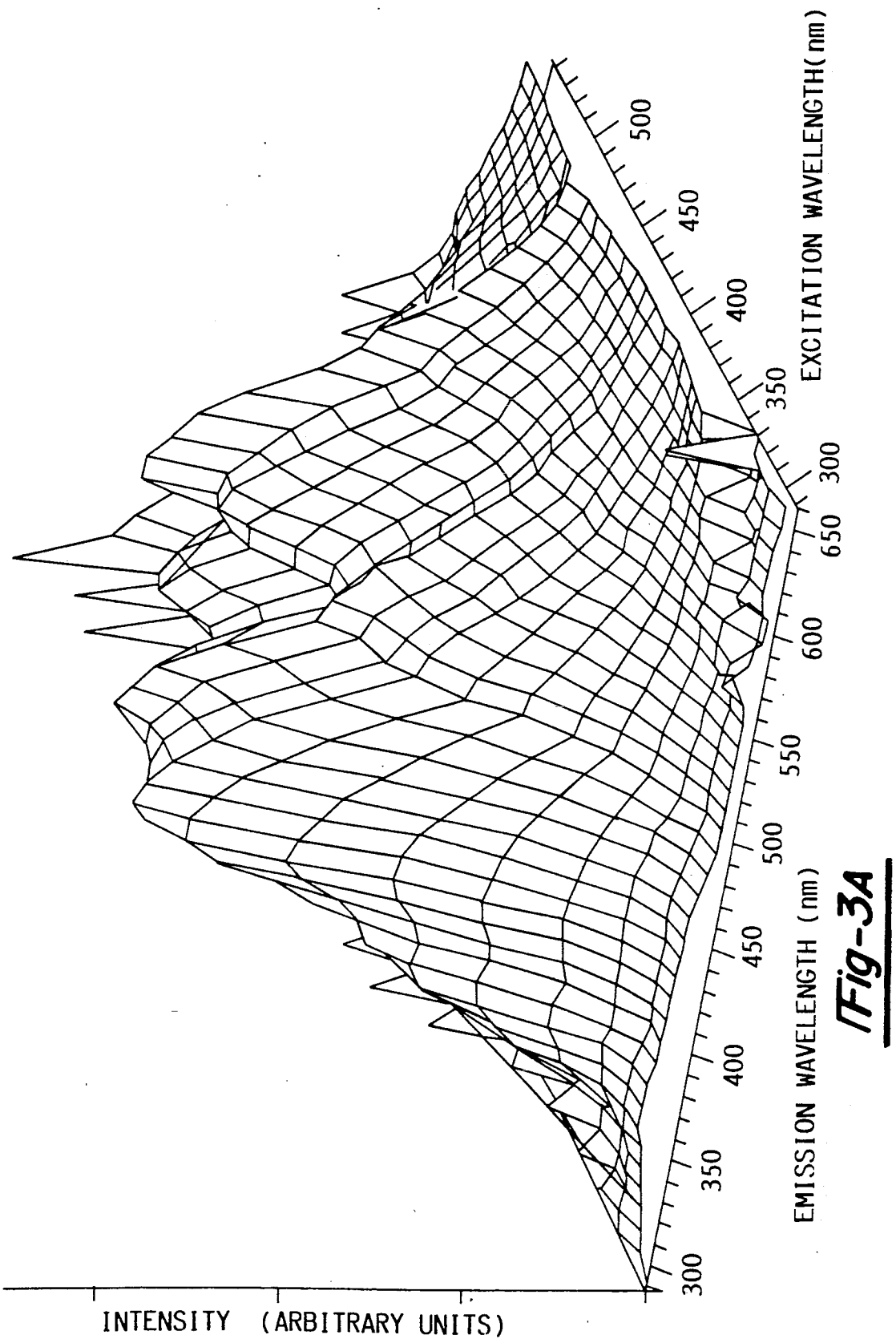
FIG. 3a is a three dimensional contour plot of a typical fluorometric measurement of media stripped of raised white plaque.
Figure 3B:
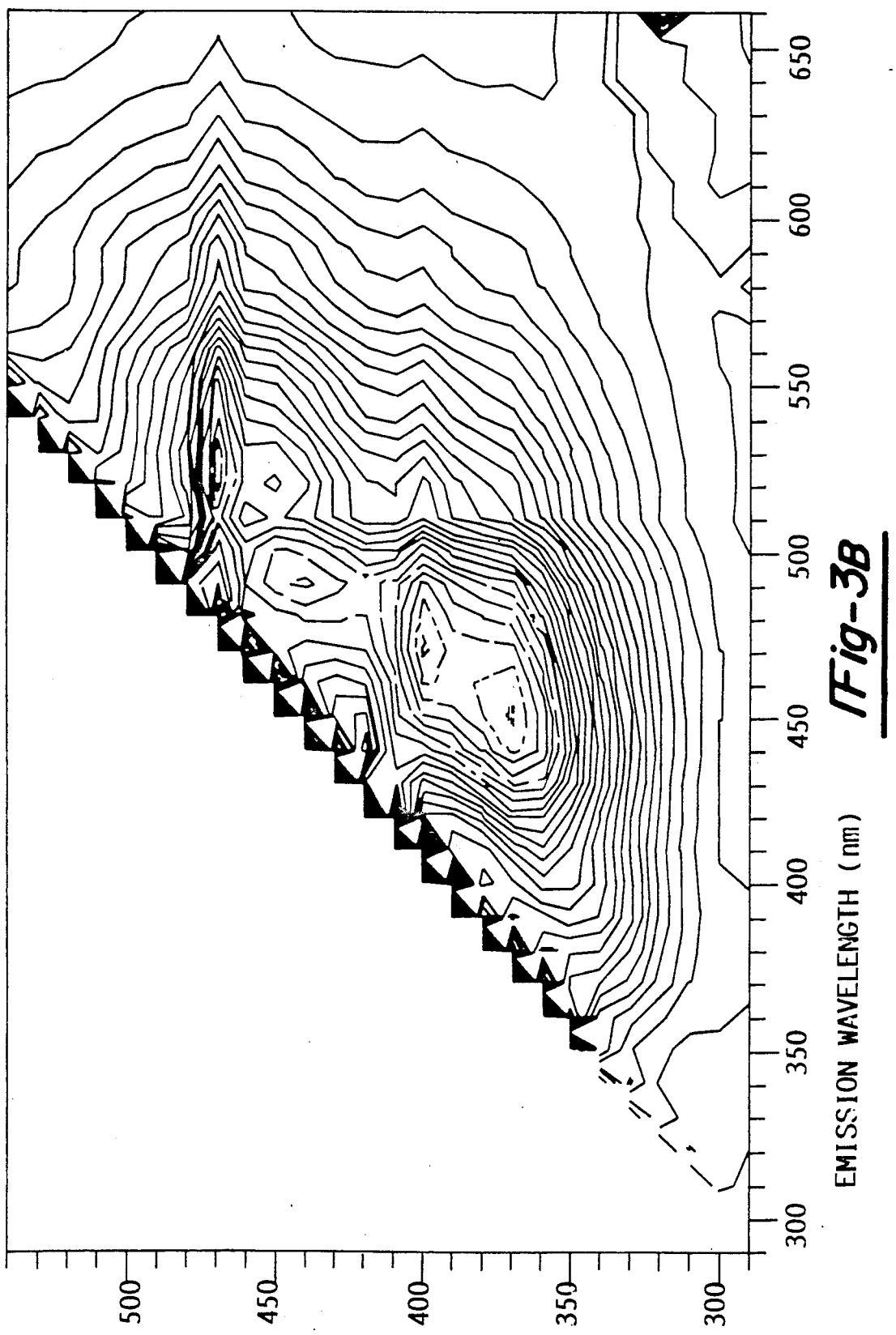

FIGS. 1a through 3b are contour plots of three typical fluorometer measurements. The contour levels were chosen to give 30 levels between 0 and maximum measured intensity. Because of the ambiguity of maximum and minimum, three dimensional plots of the same data are supplied to assist in interpreting such a format. Reflection artifacts are partially removed to allow a clear view of the structures of interest. Such reflection artifacts manifest itself in a series of triangular shaped structures running diagonally across the contour plot.

Evaluation of these plots and the other related graphs indicate that the maximum peak usually occurs in the 340–360:380–500 nm range. These maxima can be used to identify atheroma plaque and normal tissue in that normal tissue spectra demonstrate a peak at 360:430 [excitation wavelength:emission wavelength] while diseased tissue spectra has a peak at 340:380. The stripped aorta spectra has two main peaks at 370:450 and 400:480, of which the latter is not always seen and the former sometimes shifts more closely to the normal tissue peak. Graphs from the various tissues classes indicate that the degree with which the 340:380 peak dominates the plot seems to be dependent upon the class of tissue. Fatty flecked aorta; the earliest microscopically identifiable instance of atherosclerosis has almost equal intensity for both the normal and diseased peaks while raised white plaque exhibits the strongest domination of the diseased peak. In partially calcified plaques, the spectra shows a maximum intensity at the diseased peak site, but varying widely in intensity with respect to the normal peak site. It can be concluded that the calcium deposits are not a contributing factor to the diseased peak [340:380 nm] and may to some degree mask it.

In order to reduce the spectral signal to a single judgement parameter, a contrast function was tested using standard nonparametric statistical methods. The mean and standard deviation for normal and diseased tissue were calculated. From these values, the threshold boundary between normal and diseased tissue was hypothesized as being at the 99.9% upper confidence limit for the normal tissues. This definition of threshold is totally arbitrary and could be modified in this situation where either the specificity of detecting normal tissue could be lowered to enhance the sensitivity of detecting diseased samples or reversed as desired. A tally is made of the entire data set to find the number of correctly identified normal diseased tissue samples and incorrectly identified samples. From this tally, the sensitivity of the test to identify diseased tissue is defined as the number of identified diseased samples divided by the total number of diseased samples. The specificity of the test to identify normal samples correctly is defined as the number of identified normal samples divided by the total number of normal samples.

When considering fluorescence as a means of identifying plaque, it is assumed that there are biochemical differences between the diseased and normal arterial wall. These chemical differences should express themselves as specific excitation-emission wavelength peaks. The great variation in the chemical makeup of tissue from individual to individual expresses itself in the range of normal tissues which cannot be identified by a single spectral signature. Thus, for a given spectral point to be useful, as a tissue becomes more diseased, the ratio of intensities (as expressed as the contrast function) between a diseased related peak and a healthy peak must go through a single threshold beyond which no normal variation in healthy tissue can surpass. This consideration means that only one confidence limit should be considered as a threshold. In the analysis used in accordance with the present invention, any given ratio and its reverse were tested while using the only upper 99.9% confidence level.

FIG. 4 is a histogram summarizing the incidence of specificity and sensitivity wherein an order two contrast function consisting of four critical points on the emission spectrum of the common excitation wavelength met the 80% criteria for both the sensitivity and specificity. In other words, the ratio of 2 points on 2 peaks or aberrations characteristic of diseased tissue were divided by 2 points on the same spectrum at a wavelengths characteristic of structurally viable tissue to provide a specificity and sensitivity over 80%. If each incident of identification is viewed as a single possible means of identification, then combinations of the above, (higher order contrast functions) could be used to more carefully define the status of the tissue. Based on this argument, it would appear that the optimum wavelength for tissue identification is in the 350 to 390 nm range wherein sensitivity and specificity obtain values over 95%.

The number of emission wavelengths that must be measured in order to successfully identify atheroma plaque was defined. Both sensitivity and specificity should be over 95%. In angioplasty, it is necessary to identify the diseased tissue quite accurately because a surgeon does not want to perform the angioplasty additional unnecessary times. However, a surgeon is placed in the dichotomy of not wanting to irradiate normal tissue thereby possibly causing an ablation which in and of itself would irreversibly damage tissue to the extent of being lethal.

The present invention provides at least a standard with which levels of atherosclerotic disease can be identified and distinguished from normal tissue. The invention utilizes a contrast function based on intensity ratios to provide a practical alternative to existing methods of determination. The use of a single threshold also offers maximization of sensitivity and specificity to enhance accuracy of the determination and also provides an option of sacrificing either sensitivity or specificity to enhance the other by merely adjusting one parameter.

A summary of sensitivity and specificity of the second order contrast functions makes it apparent that a number of optimum wavelengths of excitation appear between 350 and 390 nm given the emission wavelengths that can be detected. This observation is derived from the relative sensitivity and specificity plots of FIG. 4.

Accordingly, the present invention utilizes an identification test based on the ratio of different fluorescent emission intensities by observations which indicate that there are a large number of possible fluorescent combinations capable of discriminating between wanted and unwanted tissue. Adding the restraint that the excitation wavelength for the test be constant, it is shown that there is an optimum excitation wavelength range between 350 and 390 nm for the identification of the unwanted tissue.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims the invention may be practiced otherwise than as specifically described.

What is claimed:

1. A method of identifying atherosclerotic plaque versus structurally viable tissue, said method including the steps of: emitting a beam of light at a single excitation wavelength of between 350 an 390 nm at a tissue; detecting an quantifying the fluorescence emission spectrum of the emitted beam at critical points of optimum distinguishing emission from atherosclerotic plaque and structurally viable tissue; and distinguishing the presence of atherosclerotic plaque from structurally viable tissue by the presence of absence of the quantity of intensity of emissions at the critical points of optimum distinguishing emission.

2. A method as set forth in claim 1 wherein said distinguishing step is reduced to a single judgement parameter by comparing the ratio of the quantity of the intensity of emission of at least two of the critical points of optimum distinguishing emission from atheroscleric plaque tissue and two critical points from normal structural tissues against a standard compilation of ratios of normal and atherosclerotic tissue, wherein a threshold limit for normal tissue, is used in identifying atherosclerotic tissue.

3. A method as set forth in claim 2 wherein the threshold is set by data at the 99.9 confidence limit of the variation in a contrast function for structurally viable tissue.

4. A method as set forth in claim 2 wherein critical points of optimum distinguishing emission from the atherosclerotic plaque are 570 and 600 nm and from the normal structural tissue at 480 and 500 nm using an excitation wavelength of 370 nm.

* * * * *